US012071520B2

(12) United States Patent
Essaddam et al.

(10) Patent No.: US 12,071,520 B2
(45) Date of Patent: *Aug. 27, 2024

(54) TEREPHTHALIC ACID ESTERS FORMATION

(71) Applicant: 9449710 CANADA INC., Terrebonne (CA)

(72) Inventors: Adel Essaddam, Terrebonne (CA); Fares Essaddam, Terrebonne (CA)

(73) Assignee: 9449710 CANADA INC., Terrebonne (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,801

(22) Filed: Jun. 10, 2022

(65) Prior Publication Data

US 2023/0125080 A1  Apr. 27, 2023

Related U.S. Application Data

(63) Continuation of application No. 17/024,159, filed on Sep. 17, 2020, now Pat. No. 11,401,398, which is a continuation of application No. 16/450,807, filed on Jun. 24, 2019, now Pat. No. 10,808,096.

(60) Provisional application No. 62/689,597, filed on Jun. 25, 2018.

(51) Int. Cl.
| | | |
|---|---|---|
| *C08J 11/22* | (2006.01) | |
| *C07C 31/30* | (2006.01) | |
| *C07C 67/03* | (2006.01) | |
| *C07C 69/82* | (2006.01) | |
| *C08J 11/24* | (2006.01) | |
| *C07C 29/132* | (2006.01) | |

(52) U.S. Cl.
CPC ............... *C08J 11/22* (2013.01); *C07C 31/30* (2013.01); *C07C 67/03* (2013.01); *C07C 69/82* (2013.01); *C08J 11/24* (2013.01); *C07C 29/132* (2013.01); *C08J 2367/02* (2013.01)

(58) Field of Classification Search
CPC ... C91J 11/22; C91J 11/24; C08F 8/50; C07C 31/30; C07C 31/202; C07C 69/82; C08L 101/00; C08J 11/22; C08J 11/24
See application file for complete search history.

(56) References Cited

U.S. PATENT DOCUMENTS

| | | | |
|---|---|---|---|
| 2,884,443 A | 4/1959 | Erhard et al. | |
| 3,219,622 A | 11/1965 | Luciano et al. | |
| 3,321,510 A | 5/1967 | Rudolf et al. | |
| 3,501,420 A | 3/1970 | Stevenson et al. | |
| 3,520,940 A | 7/1970 | Smith, Jr. et al. | |
| 4,163,860 A | 8/1979 | Delattre et al. | |
| 4,263,413 A | 4/1981 | Gardner et al. | |
| 4,355,175 A | 10/1982 | Pusztaszeri | |
| 4,525,307 A | 6/1985 | Pratt | |
| 5,045,122 A | 9/1991 | Tindall et al. | |
| 5,051,528 A | 9/1991 | Naujokas et al. | |
| 5,236,959 A | 8/1993 | Oakley et al. | |
| 5,328,982 A | 7/1994 | Tindall et al. | |
| 5,386,055 A | 1/1995 | Lee et al. | |
| 5,668,186 A | 9/1997 | Brunelle et al. | |
| 5,952,520 A | 9/1999 | Naujokas | |
| 6,528,546 B2 | 3/2003 | Lee et al. | |
| 6,670,503 B2 | 12/2003 | Broccatelli | |
| 6,706,843 B1 | 3/2004 | Ishihara et al. | |
| 6,720,448 B2 | 4/2004 | Broccatelli | |
| 6,911,546 B2 | 6/2005 | Hedrick et al. | |
| 6,916,936 B2 | 7/2005 | Hedrick et al. | |
| 7,053,221 B2 | 5/2006 | Hedrick et al. | |
| 7,462,649 B2 | 12/2008 | Nakao et al. | |
| 7,544,800 B2 | 6/2009 | Hedrick et al. | |
| 7,750,057 B2 | 7/2010 | Ogasawara | |
| 7,893,122 B2 | 2/2011 | Fregoso-Infante et al. | |
| 8,309,618 B2 | 11/2012 | Hedrick et al. | |
| 8,492,504 B2 | 7/2013 | Hedrick et al. | |
| 8,513,379 B2 | 8/2013 | Matsumura | |
| 9,550,713 B1 | 1/2017 | Essaddam | |
| 10,087,130 B2 | 10/2018 | Essaddam | |
| 10,251,976 B2 | 4/2019 | Erbe et al. | |
| 10,252,976 B1 | 4/2019 | Essaddam et al. | |
| 10,640,442 B2 | 5/2020 | Essaddam | |
| 10,793,508 B2 | 10/2020 | Essaddam et al. | |
| 10,808,096 B2 | 10/2020 | Essaddam et al. | |
| 11,248,103 B2 | 2/2022 | Essaddam et al. | |
| 11,401,398 B2 | 8/2022 | Essaddam et al. | |
| 2005/0027023 A1 | 2/2005 | Masuda et al. | |
| 2008/0242751 A1 | 10/2008 | Kurian et al. | |

(Continued)

FOREIGN PATENT DOCUMENTS

CA  2069500 A1  6/1991
CN  1585798 A  2/2005

(Continued)

OTHER PUBLICATIONS

Kouzu et al. Heterogeneous catalysis of calcium oxide used for transesterification of soybean oil with refluxing methanol. Applied Catalysis A: General 355:94-99 (2009).
Liu et al. Calcium methoxide as a solid base catalyst for the transesterification of soybean oil to biodiesel with methanol. Fuel 87:1076-1082 (2008).
Sullivan et al. Mixed plastics waste valorization through tandem chemical oxidation and biological funneling. Science 378(6616):207-211 (2022).
U.S. Appl. No. 17/350,979 Office Action dated Nov. 22, 2022.
U.S. Appl. No. 17/529,643 Office Action dated Nov. 23, 2022.
Yan. Recycling plastic using a hybrid process. Science 378(6616):132-133 (2022).
Acs. Common Organic Solvents: Table of Properties. downloaded from https://www.organicdivision.org/orig/organic_solvents.html on Apr. 4, 2018, p. 1-2).

(Continued)

*Primary Examiner* — Yate' K Cutliff
(74) *Attorney, Agent, or Firm* — WILSON SONSINI GOODRICH & ROSATI

(57) ABSTRACT

The present disclosure relates to the formation of dimethyl terephthalate (DMT). The present invention also relates to the depolymerization of polyethylene terephthalate (PET) and the recovery of dimethyl terephthalate (DMT).

18 Claims, No Drawings

(56) References Cited

U.S. PATENT DOCUMENTS

| | | |
|---|---|---|
| 2009/0032015 A1 | 2/2009 | Myllymaki et al. |
| 2009/0171113 A1 | 7/2009 | Anderson et al. |
| 2009/0318579 A1 | 12/2009 | Ikenaga |
| 2011/0004014 A1 | 1/2011 | Hedrick et al. |
| 2013/0345453 A1 | 12/2013 | Sipos et al. |
| 2015/0315325 A1 | 11/2015 | Tabor et al. |
| 2016/0237243 A1 | 8/2016 | Woldt et al. |
| 2017/0008826 A1 | 1/2017 | Essaddam |
| 2017/0113995 A1 | 4/2017 | Mastrangelo |
| 2017/0152203 A1 | 6/2017 | Essaddam |
| 2019/0084916 A1 | 3/2019 | Essaddam et al. |
| 2019/0290035 A1 | 9/2019 | Nieraad et al. |
| 2019/0390035 A1 | 12/2019 | Essaddam et al. |
| 2020/0157307 A1 | 5/2020 | Guo |
| 2020/0298219 A1 | 9/2020 | Essaddam et al. |
| 2020/0392067 A1 | 12/2020 | Essaddam et al. |
| 2021/0030960 A1 | 2/2021 | Huang et al. |
| 2021/0309601 A1 | 10/2021 | Essaddam et al. |
| 2022/0135761 A1 | 5/2022 | Essaddam et al. |
| 2023/0374249 A1 | 11/2023 | Essaddam et al. |

FOREIGN PATENT DOCUMENTS

| | | | |
|---|---|---|---|
| CN | 101628909 A | | 1/2010 |
| CN | 102746460 A | | 10/2012 |
| CN | 104327254 | * | 2/2015 |
| CN | 104327254 A | | 2/2015 |
| CN | 105601507 A | | 5/2016 |
| CN | 108047023 A | | 5/2018 |
| EP | 1710226 A1 | | 10/2006 |
| FR | 1081681 A | | 12/1954 |
| FR | 2335490 A1 | | 7/1977 |
| GB | 729803 A | | 5/1955 |
| GB | 784248 A | | 10/1957 |
| GB | 787554 A | | 12/1957 |
| GB | 901094 A | | 7/1962 |
| GB | 1043671 A | | 9/1966 |
| GB | 2041916 A | | 9/1980 |
| JP | H0488745 A | | 3/1992 |
| JP | 2000072720 A | | 3/2000 |
| JP | 2001192492 A | | 7/2001 |
| JP | 2001261707 A | | 9/2001 |
| JP | 2003055300 A | | 2/2003 |
| JP | 2006045371 A | | 2/2006 |
| JP | 2006052173 A | | 2/2006 |
| JP | 2006512460 A | | 4/2006 |
| JP | 2008063305 A | | 3/2008 |
| JP | 4365592 B2 | | 11/2009 |
| JP | 4575074 B2 | | 11/2010 |
| JP | 2012116779 A | | 6/2012 |
| JP | 2012131729 A | | 7/2012 |
| JP | 2014070132 A | | 4/2014 |
| KR | 20060127925 A | | 12/2006 |
| KR | 20180092147 A | | 8/2018 |
| WO | WO-9527753 A1 | | 10/1995 |
| WO | WO-9724310 A1 | | 7/1997 |
| WO | WO-9746611 A1 | | 12/1997 |
| WO | WO-9803459 A1 | | 1/1998 |
| WO | WO-0047659 A1 | | 8/2000 |
| WO | WO-0158982 A1 | | 8/2001 |
| WO | WO-0218471 A2 | | 3/2002 |
| WO | WO-0238276 A1 | | 5/2002 |
| WO | WO-2005003217 A1 | | 1/2005 |
| WO | WO-2006021063 A1 | | 3/2006 |
| WO | WO-2007076384 A2 | | 7/2007 |
| WO | WO-2007096326 A1 | | 8/2007 |
| WO | WO-2007113872 A1 | | 10/2007 |
| WO | WO-2007148353 A1 | | 12/2007 |
| WO | WO-2008007384 A1 | | 1/2008 |
| WO | WO-2017007965 A1 | | 1/2017 |
| WO | WO-2019051597 A1 | | 3/2019 |
| WO | WO-2020002999 A2 | | 1/2020 |
| WO | WO-2020188359 A1 | | 9/2020 |

OTHER PUBLICATIONS

Adeakin et al. Polymer-Solvent Relation: Swelling and Fibre Morphology. IOSR-JPTE 4(2):27-28 (2017).

Al-Sabagh et al. Greener routes for recycling of polyethylene terephthalate. Egyptian Journal of Petroleum 25(1):53-64 (2016).

Balcerzyk. Behavior of swollen poly(ethylene terephthalate) on the action of alkali solutions. Kolloid-Z.u.Z. Polymere 251:776-778 (1973).

Cho et al. Hydrophilic treatment of PET [poly(ethylene terephthalate)] fabric with monosodium ethylene glycolate. Journal Of The Korean Fiber Society 23(2):80-87 (1986) (English Abstract).

Falbe. Alcohols, Aliphatic—Ullmann's Encyclopedia of Industrial Chemistry. Downloaded from https://doi.org/10.1002/14356007.a01_279.pub2, first published Jan. 15, 2013, p. 1-26.

Feghali et al. Room Temperature Organocatalyzed Reductive Depolymerization of Waste Polyethers Polyesters and Polycarbonates. ChemSusChem. 8(6): 980-984 (2015).

Haga. Anomalous Swelling of Poly(ethylene terephthalate) fiber in organic solvents. Journal of Polymer Science, Polymer Letters Edition 20:629-634 (1982).

Haga. Case II swelling of poly(ethylene terephthalate) in organic solvents. Journal of Applied Polymer Science 26(8):2649-2655 (1981).

Kurokawa et al. Methanolysis of polyethylene terephthalate (PET) in the presence of aluminium tiisopropoxide catalyst to form dimethyl terephthalate and ethylene glycol. Polymer Degradation And Stability 79(3):529-533 (2003).

Mishra et al. Kinetic and thermodynamic study of methanolysis of poly(ethylene terephthalate) waste powder. Polym Int 52:337-342 (2003).

Mohsin et al. Sodium Methoxide Catalyzed Depolymerization of Waste Polyethylene Terephthalate Under Microwave Irradiation. Catalysis in Industry 10:41-48 (2018).

Mohsin et al. Sodium Methoxide Catalyzed Depolymerization of Waste Polyethylene Terephthalate under Microwave Irradiation. Kataliz V Promyshlennosti 17(4):278-286 (2017).

Namboori et al. Steric effects in the basic hydrolysis of poly(ethylene terephthalate). Journal of Applied Polymer Science 12:1999-2005 (1968).

PCT/CA2018/051135 International Search Report and Written Opinion dated Dec. 4, 2018.

PCT/IB2019/000816 International Search Report and Written Opinion dated Jan. 3, 2020.

PCT/IB2020/000216 International Search Report and Written Opinion dated Jun. 25, 2020.

PCT/US2016/041392 International Search Report and Written Opinion dated Nov. 10, 2016.

Ramsden et al. Factors Influencing the Kinetics of the Alkaline Depolymerisation of Poly(ethylene terephthalate) I: The Effect of Solvent. J Chem Tech Biotechnol 67:131-136 (1996).

Sheehan. Terephthalic Acid, Dimethyl Terephthalate, and Isophthalic Acid. Ullmann's Encyclopedia of Industrial Chemistry 36:17-28 (2011).

Shukla et al. Glycolysis of polyethylene terephthalate waste fibers. Journal of Applied Polymer Science 98:513-517 (2005).

U.S. Appl. No. 14/795,116 Office Action dated Jun. 2, 2016.
U.S. Appl. No. 15/377,460 Office Action dated Jan. 29, 2018.
U.S. Appl. No. 15/706,484 Office Action dated Apr. 13, 2018.
U.S. Appl. No. 15/706,484 Office Action dated Oct. 15, 2018.
U.S. Appl. No. 16/117,672 Office Action dated May 15, 2019.
U.S. Appl. No. 16/259,980 Office Action dated Feb. 4, 2020.
U.S. Appl. No. 16/450,807 Office Action dated Feb. 20, 2020.
U.S. Serial No. 17/024,159 Office Action dated Dec. 1, 2021.
U.S. Serial No. 17/024,159 Office Action dated Jul. 7, 2021.
U.S. Appl. No. 17/350,979 Office Action dated Aug. 10, 2022.
U.S. Appl. No. 17/350,979 Office Action dated Jan. 25, 2022.
U.S. Appl. No. 17/350,979 Office Action dated Oct. 21, 2021.
U.S. Appl. No. 16/821,870 Office Action dated Jul. 23, 2021.

Venkatachalam et al. Materials Science "Polyester"—Chapter 4: Degradation and Recyclability of Poly(Ehtylene Terephthalate). Intech 24 pgs. (2012).

(56) References Cited

OTHER PUBLICATIONS

Bae et al., The Characteristics of PET Micro Fiber Fabrics Decomposed dy Sodium Ethylene glycol Solution. Journal of the Korean Home Economics Association 36(8):95-104 (1998) (English Abstract).
U.S. Appl. No. 17/350,979 Office Action dated May 10, 2023.
U.S. Appl. No. 18/228,531 Office Action dated Sep. 20, 2023.
Ishalina, O.V., Lakeev, S.N., Minnigulov, R.Z., & Majdanova, I.O. (2015). Analysis of polyethylene terephthalate waste recycling methods. Production and use of elastomers, (3), 39-48 (in Russian). https://cyberleninka.ru/article/n/analiz-metodov-pererabotki-othodov-polietilentereftalata.

* cited by examiner

TEREPHTHALIC ACID ESTERS FORMATION

CROSS-REFERENCE

This application is a continuation of U.S. patent application Ser. No. 17/024,159, filed Sep. 17, 2020, which is a continuation of U.S. patent application Ser. No. 16/450,807, filed on Jun. 24, 2019, now U.S. Pat. No. 10,808,096, issued on Oct. 20, 2020, which claims the benefit of U.S. Provisional Application Ser. No. 62/689,597, filed Jun. 25, 2018, which are herein incorporated by reference in their entirety.

FIELD OF THE INVENTION

The present disclosure relates to the formation of ester derivatives from polyesters and more specifically to the formation of terephthalic acid esters from polyethylene terephthalate (PET). The present disclosure also relates to the formation of dimethyl terephthalate (DMT).

BACKGROUND OF THE INVENTION

The polyethylene terephthalate (PET) bottle resin market has been growing strongly as PET resins have replaced glass in carbonated soft drink, bottled water and food containers.

Dimethyl terephthalate (DMT) is primarily used in the manufacture of polyethylene terephthalate (PET) for fiber, film, container plastics, and specialty plastics applications.

The largest polyester sector is the fibers market where it is used to make clothes, home textiles such as sheets and curtains, carpets and rugs, and industrial products such as tire cord, seat belts, hoses and ropes. PET film is utilized in electrical applications such as dielectric metal foil capacitors and for food packaging.

The growth in polyester has not been converted into DMT demand. For most grades of polyester used in textiles and food and beverage containers, it is more economical to use purified terephthalic acid rather than DMT.

SUMMARY OF THE INVENTION

Disclosed herein is a process for the depolymerization of polyethylene terephthalate (PET) to form a terephthalate; the process comprising admixing polyethylene terephthalate (PET) with a mixture comprising a glycoxide.

In some embodiments of the process, the mixture further comprises a solvent.

In some embodiments of the process, the solvent is selected from methanol, ethanol, n-propanol, isopropanol, t-butanol, ethylene glycol, glycerol, cyclohexane-1,4-dimethanol, phenol, benzyl alcohol, and any combinations thereof. In some embodiments of the process, the solvent is methanol.

In some embodiments of the process, the solvent is added to the polyethylene terephthalate (PET) prior to the addition of the glycoxide.

In some embodiments of the process, the polyethylene terephthalate (PET) is mixed with the solvent prior to the addition of the glycoxide for about 15 mins to about 120 mins. In some embodiments of the process, the polyethylene terephthalate (PET) is mixed with the solvent prior to the addition of the glycoxide for about 60 min.

In some embodiments of the process, the polyethylene terephthalate (PET) is mixed with the solvent prior to the addition of the glycoxide at a temperature between about 50° C. to about 100° C. In some embodiments of the process, the polyethylene terephthalate (PET) is mixed with the solvent prior to the addition of the glycoxide at a temperature of about 60° C.

In some embodiments of the process, the terephthalate is dimethyl terephthalate (DMT).

In some embodiments of the process, the glycoxide is sodium glycoxide. In some embodiments of the process, the glycoxide is mono sodium glycoxide. In some embodiments of the process, sodium glycoxide is provided as a suspension.

In some embodiments of the process, the mono sodium glycoxide suspension is prepared by a process comprising:
   a) heating mono ethylene glycol;
   b) adding sodium hydroxide thereby forming mono sodium glycoxide;
   c) drying the mono sodium glycoxide;
   d) suspending the dried mono sodium glycoxide into a suspending solvent; and
   e) aging the suspension.

In some embodiments of the process, step (a) is performed at a temperature between about 70° C. to about 100° C. In some embodiments of the process, step (a) is performed at a temperature of about 90° C.

In some embodiments of the process, the ratio of mono sodium glycoxide to the suspending solvent is between about 0.05:1 to about 0.5:1 (mol/mol).

In some embodiments of the process, the ratio of mono sodium glycoxide to the suspending solvent is about 0.2:1 (mol/mol).

In some embodiments of the process, the suspending solvent is methanol.

In some embodiments of the process, the suspension is aged for about 1-14 days. In some embodiments of the process, the suspension is aged for about 1-7 days. In some embodiments of the process, the suspension is aged for about 7 days.

In some embodiments of the process, the ratio of glycoxide to polyethylene terephthalate (PET) is between about 1:2 and about 1:20 (mol/mol).

In some embodiments of the process, the ratio of glycoxide to polyethylene terephthalate (PET) is between about 1:5 and about 1:20 (mol/mol).

In some embodiments of the process, the ratio of glycoxide to polyethylene terephthalate (PET) is between about 1:10 and about 1:20 (mol/mol).

In some embodiments of the process, the ratio of glycoxide to polyethylene terephthalate (PET) is between about 1:10 and about 1:15 (mol/mol).

In some embodiments of the process, the terephthalate is obtained in at least about 90 mol % yield. In some embodiments of the process, the terephthalate is obtained in at least about 95 mol % yield. In some embodiments of the process, the terephthalate is obtained in at least about 99 mol % yield.

In some embodiments of the process, the process further yields mono ethylene glycol. In some embodiments of the process, the mono ethylene glycol is obtained in at least about 80 mol % yield. In some embodiments of the process, the mono ethylene glycol is obtained in at least about 85 mol % yield.

Disclosed herein is a process for the depolymerization of polyethylene terephthalate (PET) to form a terephthalate; the process comprising:
   (i) admixing the polyethylene terephthalate (PET) with a first solvent to yield a first mixture;
   (ii) adding a glycoxide to the first mixture;

(iii) adding a second solvent; and
(iv) admixing;
thereby forming the terephthalate.

In some embodiments of the process, the terephthalate is dimethyl terephthalate (DMT).

In some embodiments of the process, the first solvent is selected from methanol, ethanol, n-propanol, isopropanol, t-butanol, ethylene glycol, glycerol, cyclohexane-1,4-dimethanol, phenol, benzyl alcohol, and any combinations thereof. In some embodiments of the process, the first solvent is methanol.

In some embodiments of the process, step (i) is performed for about 15 mins to about 120 mins. In some embodiments of the process, step (i) is performed for about 60 min.

In some embodiments of the process, step (i) is performed at a temperature between about 50° C. to about 100° C. In some embodiments of the process, step (i) is performed at a temperature of about 60° C.

In some embodiments of the process, a portion of the first solvent is removed prior to step (ii) to yield a second mixture.

In some embodiments of the process, the second mixture is heated at a temperature between about 70° C. to about 100° C.

In some embodiments of the process, the second mixture is heated at a temperature of about 85° C.

In some embodiments of the process, the glycoxide is sodium glycoxide. In some embodiments of the process, the glycoxide is mono sodium glycoxide. In some embodiments of the process, the mono sodium glycoxide is provided as a suspension in a suspending solvent.

In some embodiments of the process, the mono sodium glycoxide suspension is prepared by a process comprising:
  a) heating mono ethylene glycol;
  b) adding sodium hydroxide thereby forming mono sodium glycoxide;
  c) drying the mono sodium glycoxide;
  d) suspending the dried mono sodium glycoxide in a suspending solvent; and
  e) aging the suspension.

In some embodiments of the process, step (a) is performed at a temperature between about 70° C. to about 100° C. In some embodiments of the process, step (a) is performed at a temperature of about 90° C.

In some embodiments of the process, the ratio of mono sodium glycoxide to the suspending solvent is between about 0.05:1 to about 0.5:1 (mol/mol).

In some embodiments of the process, the ratio of mono sodium glycoxide to the suspending solvent is about 0.2:1 (mol/mol).

In some embodiments of the process, the suspending solvent is methanol.

In some embodiments of the process, the suspension is aged for about 1-14 days. In some embodiments of the process, the suspension is aged for about 1-7 days. In some embodiments of the process, the suspension is aged for about 7 days.

In some embodiments of the process, the ratio of glycoxide to polyethylene terephthalate (PET) is between about 1:2 and about 1:20 (mol/mol). In some embodiments of the process, the ratio of glycoxide to polyethylene terephthalate (PET) is between about 1:5 and about 1:20 (mol/mol). In some embodiments of the process, the ratio of glycoxide to polyethylene terephthalate (PET) is between about 1:10 and about 1:20 (mol/mol). In some embodiments of the process, the ratio of glycoxide to polyethylene terephthalate (PET) is between about 1:10 and about 1:15 (mol/mol).

In some embodiments of the process, the second solvent is selected from methanol, ethanol, n-propanol, isopropanol, t-butanol, ethylene glycol, glycerol, cyclohexane-1,4-dimethanol, phenol, benzyl alcohol, and any combinations thereof. In some embodiments of the process, the second solvent is methanol.

In some embodiments of the process, step (iv) is performed for about 60 mins to about 600 mins. In some embodiments of the process, step (iv) is performed for about 360 min.

In some embodiments of the process, step (iv) is performed at a temperature between about 70° C. to about 100° C. In some embodiments of the process, step (iv) is performed at a temperature of about 85° C.

In some embodiments of the process, the process further comprises step (v) filtrating the terephthalate.

In some embodiments of the process, the terephthalate is obtained in at least about 90 mol % yield. In some embodiments of the process, the terephthalate is obtained in at least about 95 mol % yield. In some embodiments of the process, the terephthalate is obtained in at least about 99 mol % yield.

In some embodiments of the process, the process further yields mono ethylene glycol. In some embodiments of the process, the mono ethylene glycol is obtained in at least about 80 mol % yield. In some embodiments of the process, the mono ethylene glycol is obtained in at least about 85 mol % yield.

Also disclosed herein is process for preparing a mono sodium glycoxide suspension; the process comprising:
  a) heating mono ethylene glycol;
  b) adding sodium hydroxide thereby forming mono sodium glycoxide;
  c) drying the mono sodium glycoxide;
  d) suspending the dried mono sodium glycoxide into a suspending solvent; and
  e) aging the suspension.

In some embodiments of the process, step (a) is performed at a temperature between about 70° C. to about 100° C. In some embodiments of the process, step (a) is performed at a temperature of about 90° C.

In some embodiments of the process, the ratio of mono sodium glycoxide to the suspending solvent is between about 0.05:1 to about 0.5:1 (mol/mol). In some embodiments of the process, the ratio of mono sodium glycoxide to the suspending solvent is about 0.2:1 (mol/mol).

In some embodiments of the process, the suspending solvent is methanol.

In some embodiments of the process, the suspension is aged for about 1-14 days. In some embodiments of the process, the suspension is aged for about 1-7 days. In some embodiments of the process, the suspension is aged for about 7 days.

DETAILED DESCRIPTION OF THE INVENTION

Dimethyl terephthalate (DMT) is used in the production of polyesters, including polyethylene terephthalate (PET), polytrimethylene terephthalate (PTT), and polybutylene terephthalate (PBT). Because DMT is volatile, it is an intermediate in some schemes for the recycling of PET, e.g. from plastic bottles. Hydrogenation of DMT affords the diol 1,4-cyclohexanedimethanol, which is a useful monomer in the formation of polyester resins.

DMT has been produced in a number of ways. Conventionally and still of commercial value is the direct esterification of terephthalic acid. Alternatively, it is prepared by alternating oxidation and methyl-esterification steps from para-xylene via methyl para-toluate. The method for the production of DMT from para-xylene and methanol consists of four major steps: oxidation, esterification, distillation, and crystallization. A mixture of para-xylene and pare-toluic ester is oxidized with air in the presence of a transition metal catalyst (Co/Mn). The acid mixture resulting from the oxidation is esterified with methanol to produce a mixture of esters. The crude ester mixture is distilled to remove all the heavy boilers and residue produced; the lighter esters are recycled to the oxidation section. The raw DMT is then crystallized to remove DMT isomers, residual acids, and aromatic aldehydes.

An Improvement in DMT production from PET recycling: due to the growing use of PET and PETG in the packaging and fiber (carpet and other textile) industries there is a need for an efficient, low energy, high yielding, and cost effective way to form DMT from PET or PETG.

Polyesters

Described herein is a process for the transformation of a polyester into an ester derivative; the process comprising admixing the polyester with a mixture comprising a glycoxide.

In some embodiments, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly(3-hydroxybutyrate-co-3-hydroxyvalerate) (PHBV), polybutylene terephthalate (PBT), polytrimethylene terephthalate (PTT), polyethylene naphthalate (PEN), Vectran®, cutin, and any combinations thereof.

In some embodiments, the polyester is polyethylene terephthalate (PET):

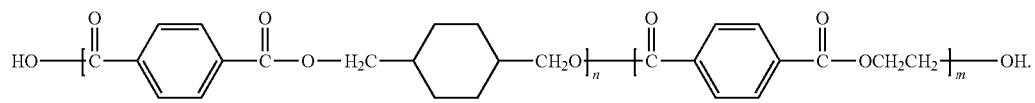

In some embodiments, the polyester is a terephthalic acid/ethylene glycol oligomer.

In some embodiments, the polyester is poly(ethylene glycol-co-1,4-cyclohexanedimethanol terephthalate) (PETG):

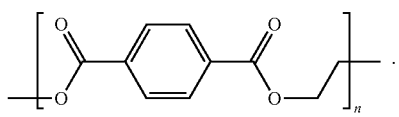

In some embodiments, the polyester is polyglycolide or polyglycolic acid (PGA),

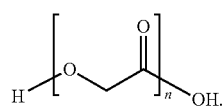

In some embodiments, the polyester is polylactic acid (PLA):

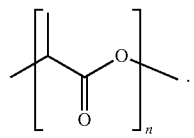

In some embodiments, the polyester is polycaprolactone (PCL):

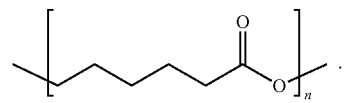

In some embodiments, the polyester is polyhydroxybutyrate (PHB):

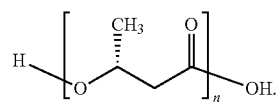

In some embodiments, the polyester is polyethylene adipate (PEA):

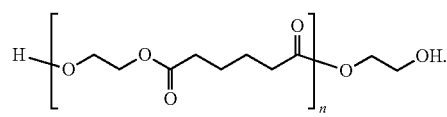

In some embodiments, the polyester is polybutylene succinate (PBS):

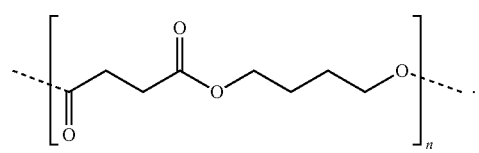

In some embodiments, the polyester is poly(3-hydroxybutyrate-co-3-hydroxyvalerate) (PHBV):

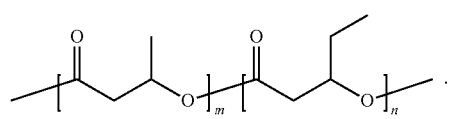

In some embodiments, the polyester is polybutylene terephthalate (PBT):

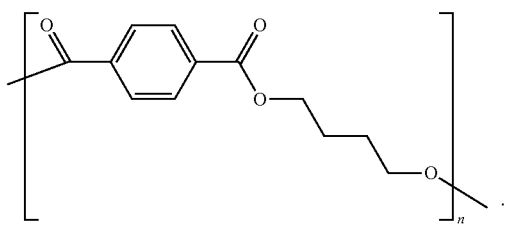

In some embodiments, the polyester is polytrimethylene terephthalate (PTT):

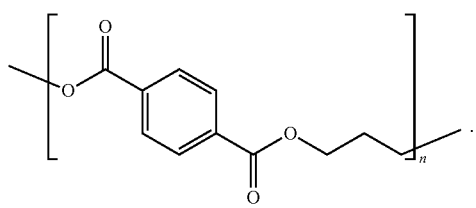

In some embodiments, the polyester is polyethylene naphthalate (PEN):

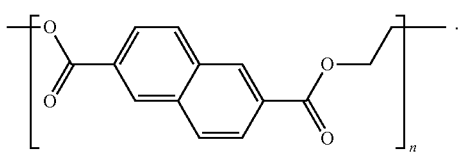

In some embodiments, the polyester is Vectran®:

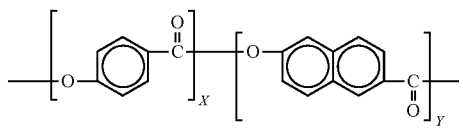

In some embodiments, the polyester is cutin. Cutin is one of two waxy polymers that are the main components of the plant cuticle, which covers all aerial surfaces of plants. Cutin consists of omega hydroxy acids and their derivatives, which are interlinked via ester bonds, forming a polyester polymer. There are two major monomer families of cutin, the C16 and C18 families. The C16 family consists mainly of 16-hydroxy palmitic acid and 9,16- or 10,16-dihydroxypalmitic acid. The C18 family consists mainly of 18-hydroxy oleic acid, 9,10-epoxy-18-hydroxy stearic acid, and 9,10, 18-trihydroxystearate. Tomato cutin consists of 16-hydroxy palmitic acid and 10,16-dihydroxypalmitic acid where the 10-isomer is largely dominant. The tomato cutin is a polyester biopolymer interesterificated. The significant proportion of secondary esters (esterification in the C-10 secondary hydroxyl) shows that the polyester structure is significantly branched.

Ester Derivatives

Described herein is a process for the transformation of a polyester into an ester derivative; the process comprising admixing the polyester with a mixture comprising a glycoxide.

In some embodiments, the polyester is polyglycolide or polyglycolic acid (PGA) and the ester derivative is a 2-hydroxyacetate derivative. In some embodiments, the ester derivative is methyl 2-hydroxyacetate.

In some embodiments, the polyester is polylactic acid (PLA) and the ester derivative is a 2-hydroxypropanoate derivative. In some embodiments, the ester derivative is methyl 2-hydroxypropanoate.

In some embodiments, the polyester is polycaprolactone (PCL) and the ester derivative is a 6-hydroxyhexanoate derivative. In some embodiments, the ester derivative is a methyl 6-hydroxyhexanoate.

In some embodiments, the polyester is polyhydroxybutyrate (PHB) and the ester derivative is a hydroxybutyrate derivative. In some embodiments, the ester derivative is methyl hydroxybutyrate.

In some embodiments, the polyester is polyethylene adipate (PEA) and the ester derivative is an adipate derivative. In some embodiments, the ester derivative is dimethyl adipate.

In some embodiments, the polyester is polybutylene succinate (PBS) and the ester derivative is a succinate derivative. In some embodiments, the ester derivative is dimethyl succinate.

In some embodiments, the polyester is poly(3-hydroxybutyrate-co-3-hydroxyvalerate) (PHBV) and the ester derivative is a hydroxybutyrate derivative, a hydroxyvalerate derivative, or a combination thereof. In some embodiments, the ester derivative is methyl hydroxybutyrate, methyl hydroxyvalerate, or a combination thereof.

In some embodiments, the polyester is polyethylene naphthalate (PEN) and the ester derivative is a naphthalate derivative. In some embodiments, the ester derivative is dimethyl naphthalate.

In some embodiments, the polyester is vectran and the ester derivative is a naphthoate derivative, a benzoate derivative, or a combination thereof. In some embodiments, the ester derivative is methyl hydroxynaphthoate or methyl hydroxybenzoate.

In some embodiments, the polyester is cutin and the ester derivative is a hydroxypalmitate or a dihydroxypalmitate derivative. In some embodiments, the ester derivative is methyl hydroxypalmitate or methyl dihydroxypalmitate.

In some embodiments, the polyester is polyethylene terephthalate (PET), poly(ethylene glycol-co-1,4-cyclohexanedimethanol terephthalate) (PETG), polytrimethylene terephthalate (PTT), or polybutylene terephthalate (PBT) and the ester derivative is aterephthalate. In some embodiments, the terephthalate is dimethyl terephthalate. In some embodiments, the terephthalate is diethyl terephthalate.

In some embodiments, the ester derivative contains less than about 10% impurity (w/w). In some embodiments, the ester derivative contains less than about 9% impurity (w/w). In some embodiments, the ester derivative contains less than about 8% impurity (w/w). In some embodiments, the ester derivative contains less than about 7% impurity (w/w). In some embodiments, the ester derivative contains less than about 6% impurity (w/w). In some embodiments, the ester derivative contains less than about 5% impurity (w/w). In some embodiments, the ester derivative contains less than about 4% impurity (w/w). In some embodiments, the ester derivative contains less than about 3% impurity (w/w). In some embodiments, the ester derivative contains less than about 2% impurity (w/w). In some embodiments, the ester derivative contains less than about 1% impurity (w/w). In some embodiments, the ester derivative contains less than about 0.5% impurity (w/w). In some embodiments, the ester derivative contains less than about 0.4% impurity (w/w). In some embodiments, the ester derivative contains less than about 0.3% impurity (w/w). In some embodiments, the ester derivative contains less than about 0.2% impurity (w/w). In some embodiments, the ester derivative contains less than about 0.1% impurity (w/w).

In some embodiments, the ester derivative contains less than about 250 ppm of any metals, less than about 240 ppm of any metals, less than about 230 ppm of any metals, less than about 220 ppm of any metals, less than about 210 ppm of any metals, less than about 200 ppm of any metals, less than about 190 ppm of any metals, less than about 180 ppm of any metals, less than about 170 ppm of any metals, less than about 160 ppm of any metals, less than about 150 ppm of any metals, less than about 140 ppm of any metals, less than about 130 ppm of any metals, less than about 120 ppm of any metals, less than about 110 ppm of any metals, less than about 100 ppm of any metals, less than about 90 ppm of any metals, less than about 80 ppm of any metals, less than about 70 ppm of any metals, less than about 60 ppm of any metals, less than about 50 ppm of any metals, less than about 40 ppm of any metals, less than about 30 ppm of any metals, less than about 20 ppm of any metals, less than about 10 ppm of any metals, less than about 5 ppm of any metals, less than about 4 ppm of any metals, less than about 3 ppm of any metals, less than about 2 ppm of any metals, less than about 1 ppm of any metals, less than about 0.9 ppm of any metals, less than about 0.8 ppm of any metals, less than about 0.7 ppm of any metals, less than about 0.6 ppm of any metals, less than about 0.5 ppm of any metals, less than about 0.4 ppm of any metals, less than about 0.3 ppm of any metals, less than about 0.2 ppm of any metals, less than about 0.1 ppm of any metals, less than about 0.09 ppm of any metals, less than about 0.08 ppm of any metals, less than about 0.07 ppm of any metals, less than about 0.06 ppm of any metals, less than about 0.05 ppm of any metals, less than about 0.04 ppm of any metals, less than about 0.03 ppm of any metals, less than about 0.02 ppm of any metals, or less than about 0.01 ppm of any metals.

In some embodiments, the ester derivative contains less than about 10 ppm of glycoxide, less than about 5 ppm of glycoxide, less than about 4 ppm of glycoxide, less than about 3 ppm of glycoxide, less than about 2 ppm of glycoxide, less than about 1 ppm of glycoxide, less than about 0.9 ppm of glycoxide, less than about 0.8 ppm of glycoxide, less than about 0.7 ppm of glycoxide, less than about 0.6 ppm of glycoxide, less than about 0.5 ppm of glycoxide, less than about 0.4 ppm of glycoxide, less than about 0.3 ppm of glycoxide, less than about 0.2 ppm of glycoxide, less than about 0.1 ppm of glycoxide, less than about 0.09 ppm of glycoxide, less than about 0.08 ppm of glycoxide, less than about 0.07 ppm of glycoxide, less than about 0.06 ppm of glycoxide, less than about 0.05 ppm of glycoxide, less than about 0.04 ppm of glycoxide, less than about 0.03 ppm of glycoxide, less than about 0.02 ppm of glycoxide, or less than about 0.01 ppm of glycoxide.

In some embodiments, the ester derivative is obtained in between about 80 and about 99 mol % yield. In some embodiments, the ester derivative is obtained in between about 85 and about 99 mol % yield. In some embodiments, the ester derivative is obtained in between about 90 and about 99 mol % yield. In some embodiments, the ester derivative is obtained in at least about 90 mol % yield. In some embodiments, the ester derivative is obtained in at least about 95 mol % yield. In some embodiments, the ester derivative is obtained in at least about 99 mol % yield.

In some embodiments, the terephthalate is obtained in between about 80 and about 99 mol % yield. In some embodiments, the terephthalate is obtained in between about 85 and about 99 mol % yield. In some embodiments, the terephthalate is obtained in between about 90 and about 99 mol % yield. In some embodiments, the terephthalate is obtained in at least about 80 mol % yield. In some embodiments, the terephthalate is obtained in at least about 85 mol % yield. In some embodiments, the terephthalate is obtained in at least about 90 mol % yield. In some embodiments, the terephthalate is obtained in at least about 95 mol % yield. In some embodiments, the terephthalate is obtained in at least about 99 mol % yield.

Glycol

Described herein is a process for the transformation of a polyester into an ester derivative and a glycol; the process comprising admixing the polyester with a mixture comprising a glycoxide. In some embodiments, the glycol is mono ethylene glycol (MEG) (or ethylene glycol). In some embodiments, the glycol is propylene glycol. In some embodiments, the glycol is butylene glycol.

In some embodiments, the glycol is obtained in between about 80 and about 99 mol % yield. In some embodiments, the glycol is obtained in between about 85 and about 99 mol % yield. In some embodiments, the glycol is obtained in between about 90 and about 99 mol % yield. In some embodiments, the glycol is obtained in at least about 80 mol % yield. In some embodiments, the glycol is obtained in at least about 85 mol % yield. In some embodiments, the glycol is obtained in at least about 90 mol % yield. In some embodiments, the glycol is obtained in at least about 95 mol % yield.

Glycoxide

In some embodiments, the process described herein comprises an alkoxide which is derived from an alcohol with a boiling point higher than water. In some embodiments, the alcohol is mono ethylene glycol (MEG), glycerol, sorbitol, 1,3-propanediol, or cyclohexane-1,4-dimethanol. In some embodiments, the alcohol is mono ethylene glycol (MEG).

In some embodiments, the process described herein comprises an alkoxide which is cost efficient. In some embodiments, the process described herein comprises the use of an alkoxide in an amount that provides a cost savings compared to other catalysts such as sodium methoxide as a weight-weight ratio. In some embodiments, the process described herein comprises the use of sodium glycoxide in an amount that provides a cost savings compared to other catalysts such as sodium methoxide as a weight-weight ratio. In some embodiments, the process described herein comprises an alkoxide that is able to undergo an exchange with methanol to results in sodium methoxide.

In some embodiments, the process described herein comprises a glycoxide. In some embodiments, the process described herein comprises a catalytic amount of a glycoxide. In some embodiments, the process described herein comprises a sub-stoichiometric amount of a glycoxide.

"Sub-stoichiometric amount", as used herein, is used to indicate that the amount of material used is less than a stoichiometric amount. The term is used herein interchangeably with "catalytic amount." In some embodiments, a sub-stoichiometric amount is less than or equal to about 95% of a stoichiometric amount. In some embodiments, a sub-stoichiometric amount is less than or equal to about 90% of a stoichiometric amount. In some embodiments, a sub-stoichiometric amount is less than or equal to about 85% of a stoichiometric amount. In some embodiments, a sub-stoichiometric amount is less than or equal to about 80% of a stoichiometric amount. In some embodiments, a sub-stoichiometric amount is less than or equal to about 75% of a stoichiometric amount. In some embodiments, a substoichiometric amount is less than or equal to about 70% of a stoichiometric amount. In some embodiments, a substoichiometric amount is less than or equal to about 65% of a stoichiometric amount. In some embodiments, a substoichiometric amount is less than or equal to about 60% of a stoichiometric amount. In some embodiments, a substoichiometric amount is less than or equal to about 55% of a stoichiometric amount. In some embodiments, a substoichiometric amount is less than or equal to about 50% of a stoichiometric amount. In some embodiments, a substoichiometric amount is less than or equal to about 45% of a stoichiometric amount. In some embodiments, a substoichiometric amount is less than or equal to about 40% of a stoichiometric amount. In some embodiments, a substoichiometric amount is less than or equal to about 35% of a stoichiometric amount. In some embodiments, a substoichiometric amount is less than or equal to about 30% of a stoichiometric amount. In some embodiments, a substoichiometric amount is less than or equal to about 25% of a stoichiometric amount. In some embodiments, a substoichiometric amount is less than or equal to about 20% of a stoichiometric amount. In some embodiments, a substoichiometric amount is less than or equal to about 15% of a stoichiometric amount. In some embodiments, a substoichiometric amount is less than or equal to about 10% of a stoichiometric amount.

"Stoichiometric amount", as used herein, is used to indicate that the amount of material used is equivalent to the number of ester linkages present in the polyester.

In some embodiments, the glycoxide, which comprises a glycoxide anion and a cation, is selected from an alkali metal glycoxide, an alkaline earth metal glycoxide, a metal glycoxide, an ammonium glycoxide, and any combinations thereof. In some embodiments, the cation is lithium, sodium, potassium, magnesium, calcium, strontium, barium, zinc, aluminum, or ammonium. In some embodiments, the glycoxide is sodium glycoxide. In some embodiments, the glycoxide is mono sodium glycoxide.

In some embodiments, the glycoxide is generated by addition of an alkali metal, an alkaline earth metal, or a metal to mono ethylene glycol (MEG). In some embodiments, the glycoxide is generated by addition of sodium hydroxyde to mono ethylene glycol (MEG).

In some embodiments, the glycoxide is provided as a suspension.

Disclosed herein is a process for preparing a mono sodium glycoxide suspension, the process comprising:
  a) heating mono ethylene glycol;
  b) adding sodium hydroxide thereby forming mono sodium glycoxide;
  c) drying the mono sodium glycoxide;
  d) suspending the dried mono sodium glycoxide into a suspending solvent; and
  e) aging the suspension.

In some embodiments, the suspending solvent is an alcohol. In some embodiments, the suspending solvent is methanol.

In some embodiments, step (a) is performed at a temperature between about 70° C. to about 100° C. In some embodiments, step (a) is performed at a temperature between about 70° C. to about 90° C. In some embodiments, step (a) is performed at a temperature between about 80° C. to about 100° C. In some embodiments, step (a) is performed at a temperature of about 70° C., about 75° C., about 80° C., about 85° C., about 90° C., about 95° C., or about 100° C. In some embodiments, step (a) is performed at a temperature of about 90° C.

In some embodiments, the ratio of mono sodium glycoxide to the suspending solvent is between about 0.05:1 to about 0.5:1 (mol/mol). In some embodiments, the ratio of mono sodium glycoxide to the suspending solvent is between about 0.1:1 to about 0.5:1 (mol/mol). In some embodiments, the ratio of mono sodium glycoxide to the suspending solvent is between about 0.1:1 to about 0.3:1 (mol/mol). In some embodiments, the ratio of mono sodium glycoxide to the suspending solvent is about 0.05:1 (mol/mol), about 0.06:1 (mol/mol), about 0.07:1 (mol/mol), about 0.08:1 (mol/mol), about 0.09:1 (mol/mol), about 0.1:1 (mol/mol), about 0.11:1 (mol/mol), about 0.12:1 (mol/mol), about 0.13:1 (mol/mol), about 0.14:1 (mol/mol), about 0.15:1 (mol/mol), about 0.16:1 (mol/mol), about 0.17:1 (mol/mol), about 0.18:1 (mol/mol), about 0.19:1 (mol/mol), about 0.2:1 (mol/mol), about 0.21:1 (mol/mol), about 0.22:1 (mol/mol), about 0.23:1 (mol/mol), about 0.24:1 (mol/mol), about 0.25:1 (mol/mol), about 0.26:1 (mol/mol), about 0.27:1 (mol/mol), about 0.28:1 (mol/mol), about 0.29:1 (mol/mol), about 0.30:1 (mol/mol), about 0.35:1 (mol/mol), about 0.40:1 (mol/mol), about 0.45:1 (mol/mol), or about 0.5:1 (mol/mol). In some embodiments, the ratio of mono sodium glycoxide to the suspending solvent is about 0.2:1 (mol/mol).

In some embodiments, the ratio of glycoxide to polyethylene terephthalate (PET) is between about 1:2 and about 1:20 (mol/mol). In some embodiments, the ratio of glycoxide to polyethylene terephthalate (PET) is between about 1:2 and about 1:10 (mol/mol). In some embodiments, the ratio of glycoxide to polyethylene terephthalate (PET) is between about 1:2 and about 1:6 (mol/mol). In some embodiments, the ratio of glycoxide to polyethylene terephthalate (PET) is between about 1:5 and about 1:20 (mol/mol). In some embodiments, the ratio of glycoxide to polyethylene terephthalate (PET) is between about 1:10 and about 1:20 (mol/mol). In some embodiments, the ratio of glycoxide to polyethylene terephthalate (PET) is between about 1:10 and about 1:15 (mol/mol). In some embodiments, the ratio of glycoxide to polyethylene terephthalate (PET) is about 1:2 (mol/mol), about 1:3 (mol/mol), about 1:4 (mol/mol), about 1:5 (mol/mol), about 1:6 (mol/mol), about 1:7 (mol/mol), about 1:8 (mol/mol), about 1:9 (mol/mol), about 1:10 (mol/mol), about 1:11 (mol/mol), about 1:12 (mol/mol), about 1:13 (mol/mol), about 1:14 (mol/mol), about 1:15 (mol/mol), about 1:16 (mol/mol), about 1:17 (mol/mol), about 1:18 (mol/mol), about 1:19 (mol/mol), or about 1:2 (mol/mol).

In some embodiments, the mono sodium glycoxide is dried to remove water formed during the reaction. In some embodiments, the mono sodium glycoxide is dried at a temperature higher than the boiling point of water. In some embodiments, the mono sodium glycoxide is dried at a temperature between about 100° C. and about 150° C. In some embodiments, the mono sodium glycoxide is dried at a temperature between about 110° C. and about 140° C. In some embodiments, the mono sodium glycoxide is dried at a temperature between about 120° C. and about 130° C. In some embodiments, the mono sodium glycoxide is dried at a temperature of about 100° C., about 105° C., about 110° C., about 115° C., about 120° C., about 125° C., about 130° C., about 135° C., about 140° C., about 145° C., or about 150° C. In some embodiments, the mono sodium glycoxide is dried at about 130° C.

In some embodiments, the suspension is aged for about 1 day to about 2 months. In some embodiments, the suspension is aged for about 1-14 days. In some embodiments, the suspension is aged for about 7-14 days. In some embodiments, the suspension is aged for about 5-8 days. In some embodiments, the suspension is aged for about 1-7 days. In some embodiments, the suspension is aged for about 1 day, about 2 days, about 3 days, about 4 days, about 5 days, about 6 days, about 7 days, about 8 days, about 9 days, about 10 days, about 11 days, about 12 days, about 13 days, or about 14 days. In some embodiments, the suspension is aged for about 7 days. In some embodiments, "aged" as used herein means stored at room temperature and ambient pressure. In some embodiments, the aging step allows for a fraction of the sodium glycoxide to convert to sodium methoxide. In some embodiments, the aged glycoxide suspension comprises up to about 85% of sodium methoxide. In some embodiments, the aged glycoxide suspension comprises up to about 85%, up to about 80%, up to about 75%, up to about 70%, up to about 65%, up to about 60%, up to about 55%, up to about 50%, up to about 45%, up to about 40%, up to about 45%, up to about 40%, up to about 35%, up to about 30%, up to about 25%, up to about 20%, up to about 15%, up to about 10%, or up to about 5% of sodium methoxide.

Depolymerization

Described herein is a process for the transformation of a polyester into an ester derivative; the process comprising admixing the polyester with a mixture comprising a glycoxide. Described herein is process for the depolymerization of polyethylene terephthalate (PET) to form a terephthalate; the process comprising admixing polyethylene terephthalate (PET) with a mixture comprising a glycoxide.

In some embodiments, the mixture further comprises a solvent.

In some embodiments, the solvent comprises a linear alcohol, branched alcohol, cyclic alcohol, or any combinations thereof. In some embodiments, the solvent is selected from methanol, ethanol, n-propanol, isopropanol, t-butanol, ethylene glycol, glycerol, cyclohexane-1,4-dimethanolphenol, benzyl alcohol, and any combinations thereof.

In some embodiments, the solvent is a linear $C_1$-$C_4$ alcohol. In some embodiments, the solvent is methanol, ethanol, propanol, butanol, or a combination thereof. In some embodiments, the solvent is methanol, ethanol, propanol, or a combination thereof. In some embodiments, the solvent is methanol. In some embodiments, the alcohol is ethanol. In some embodiments, the solvent is a branched $C_3$-$C_4$ alcohol. In some embodiments, the solvent is t-butanol, s-butanol, i-butanol, i-propanol, or any combinations thereof. In some embodiments, the solvent is a cyclic $C_3$-$C_8$ alcohol. In some embodiments, the solvent is cyclopropanol, cyclobutanol, cyclopentanol, cyclohexanol, cycloheptanol, cyclohexane-1,4-dimethanol, or any combinations thereof. In some embodiments, the solvent is cyclohexane-1,4-dimethanol.

In some embodiments, the solvent is a polyol. In some embodiments, the solvent is selected from ethylene glycol, glycerol, and any combinations thereof. In some embodiments, the solvent is selected from phenol, benzyl alcohol, and any combinations thereof.

In some embodiments, the solvent is added to the polyethylene terephthalate (PET) prior to the addition of the glycoxide. In some embodiments, the polyethylene terephthalate (PET) is mixed with the solvent prior to the addition of the glycoxide for about 15 mins to about 120 mins. In some embodiments, the polyethylene terephthalate (PET) is mixed with the solvent prior to the addition of the glycoxide for about 15 mins to about 90 mins. In some embodiments, the polyethylene terephthalate (PET) is mixed with the solvent prior to the addition of the glycoxide for about 30 mins to about 90 mins. In some embodiments, the polyethylene terephthalate (PET) is mixed with the solvent prior to the addition of the glycoxide for about 45 mins to about 90 mins. In some embodiments, the polyethylene terephthalate (PET) is mixed with the solvent prior to the addition of the glycoxide for about 15 mins, about 20 mins, about 25 mins, about 30 mins, about 35 mins, about 40 mins, about 45 mins, about 50 mins, about 55 mins, about 60 mins, about 65 mins, about 70 mins, about 75 mins, about 80 mins, about 85 mins, about 90 mins, about 95 mins, about 100 mins, about 105 mins, about 110 mins, about 115 mins, or about 120 mins. In some embodiments, the polyethylene terephthalate (PET) is mixed with the solvent prior to the addition of the glycoxide for about 60 min.

In some embodiments, the polyethylene terephthalate (PET) is mixed with the solvent prior to the addition of the glycoxide and heated to a temperature between about 50° C. to about 100° C. In some embodiments, the polyethylene terephthalate (PET) is mixed with the solvent prior to the addition of the glycoxide and heated to a temperature between about 50° C. to about 90° C. In some embodiments, the polyethylene terephthalate (PET) is mixed with the solvent prior to the addition of the glycoxide and heated to a temperature between about 50° C. to about 80° C. In some embodiments, the polyethylene terephthalate (PET) is mixed with the solvent prior to the addition of the glycoxide and heated to a temperature between about 50° C. to about 70° C. In some embodiments, the polyethylene terephthalate (PET) is mixed with the solvent prior to the addition of the glycoxide and heated to a temperature of about 50° C., about 55° C., about 60° C., about 65° C., about 70° C., about 75° C., about 80° C., about 85° C., about 90° C., about 95° C., or about 100° C. In some embodiments, the polyethylene terephthalate (PET) is mixed with the solvent prior to the addition of the glycoxide and heated to a temperature of about 60° C.

Described herein is a process for the transformation of a polyester into an ester derivative; the process comprising:
  (i) admixing the polyethylene terephthalate (PET) with a first solvent to yield a first mixture;
  (ii) adding a glycoxide to the first mixture;
  (iii) adding a second solvent; and
  (iv) admixing;
  thereby forming the ester derivative.

Also described herein is a process for the depolymerization of polyethylene terephthalate (PET) to form a terephthalate; the process comprising:
  (i) admixing the polyethylene terephthalate (PET) with a first solvent to yield a first mixture;
  (ii) adding a glycoxide to the first mixture;
  (iii) adding a second solvent; and
  (iv) admixing;
  thereby forming the terephthalate.

In some embodiments, the first solvent comprises a linear alcohol, branched alcohol, cyclic alcohol, or any combinations thereof. In some embodiments, the first solvent is selected from methanol, ethanol, n-propanol, isopropanol, t-butanol, ethylene glycol, glycerol, cyclohexane-1,4-dimethanol, phenol, benzyl alcohol, and any combinations thereof.

In some embodiments, the first solvent is a linear $C_1$-$C_4$ alcohol. In some embodiments, the first solvent is methanol, ethanol, propanol, butanol, or a combination thereof. In some embodiments, the first solvent is methanol, ethanol, propanol, or a combination thereof. In some embodiments, the first solvent is methanol. In some embodiments, the alcohol is ethanol. In some embodiments, the first solvent is a branched $C_3$-$C_4$ alcohol. In some embodiments, the first solvent is t-butanol, s-butanol, i-butanol, propanol, or any combinations thereof. In some embodiments, the first solvent is a cyclic $C_3$-$C_8$ alcohol. In some embodiments, the first solvent is cyclopropanol, cyclobutanol, cyclopentanol, cyclohexanol, cycloheptanol, cyclohexane-1,4-dimethanol, or any combinations thereof. In some embodiments, the first solvent is cyclohexane-1,4-dimethanol.

In some embodiments, the first solvent is a polyol. In some embodiments, the first solvent is selected from ethylene glycol, glycerol, and any combinations thereof. In some embodiments, the first solvent is selected from phenol, benzyl alcohol, and any combinations thereof.

In some embodiments, step (i) is performed for about 15 mins to about 120 mins. In some embodiments, step (i) is performed for about 15 mins to about 90 mins. In some embodiments, step (i) is performed for about 30 mins to about 90 mins. In some embodiments, step (i) is performed for about 45 mins to about 90 mins. In some embodiments, step (i) is performed for about 15 mins, about 20 mins, about 25 mins, about 30 mins, about 35 mins, about 40 mins, about 45 mins, about 50 mins, about 55 mins, about 60 mins, about 65 mins, about 70 mins, about 75 mins, about 80 mins, about 85 mins, about 90 mins, about 95 mins, about 100 mins, about 105 mins, about 110 mins, about 115 mins, or about 120 mins. In some embodiments, step (i) is performed for about 60 mins.

In some embodiments, step (i) is performed at a temperature between about 50° C. to about 100° C. In some embodiments, step (i) is performed at a temperature between about 50° C. to about 90° C. In some embodiments, step (i) is performed at a temperature between about 50° C. to about 80° C. In some embodiments, step (i) is performed at a temperature between about 50° C. to about 70° C. In some embodiments, step (i) is performed at a temperature of about 50° C., about 55° C., about 60° C., about 65° C., about 70° C., about 75° C., about 80° C., about 85° C., about 90° C., about 95° C., or about 100° C. In some embodiments, step (i) is performed at a temperature of about 60° C.

In some embodiments, a portion of the first solvent is removed prior to step (ii) to yield a second mixture. In some embodiments, the removal of a portion of the first solvent allows for the removal of the water trapped in the polyethylene terephthalate (PET) feedstock. In some embodiments, between about 1 mol and about 5 mol of first solvent is removed per mol of PET. In some embodiments, between about 1 mol and about 3 mol of first solvent is removed per mol of PET. In some embodiments, between about 2 mol and about 4 mol of first solvent is removed per mol of PET. In some embodiments, about 1 mol, about 1.1 mol, about 1.2 mol, about 1.3 mol, about 1.4 mol, about 1.5 mol, about 1.6 mol, about 1.7 mol, about 1.8 mol, about 1.9 mol, about 2 mol, about 2.1 mol, about 2.2 mol, about 2.3 mol, about 2.4 mol, about 2.5 mol, about 2.6 mol, about 2.7 mol, about 2.8 mol, about 2.9 mol, about 3 mol, about 3.1 mol, about 3.2 mol, about 3.3 mol, about 3.4 mol, about 3.5 mol, about 3.6 mol, about 3.7 mol, about 3.8 mol, about 3.9 mol, about 4 mol, about 4.1 mol, about 4.2 mol, about 4.3 mol, about 4.4 mol, about 4.5 mol, about 4.6 mol, about 4.7 mol, about 4.8 mol, about 4.9 mol, or about 5 mol of first solvent is removed per mol of PET.

In some embodiments, the second mixture is heated at a temperature between about 70° C. to about 100° C. In some embodiments, the second mixture is heated at a temperature between about 80° C. to about 100° C. In some embodiments, the second mixture is heated at a temperature between about 70° C. to about 90° C. In some embodiments, the second mixture is heated at a temperature of about 70° C., about 75° C., about 80° C., about 85° C., about 90° C., about 95° C., or about 100° C. In some embodiments, the second mixture is heated at a temperature of about 85° C.

In some embodiments, the second solvent comprises a linear alcohol, branched alcohol, cyclic alcohol, or any combinations thereof. In some embodiments, the second solvent is selected from methanol, ethanol, n-propanol, isopropanol, t-butanol, ethylene glycol, glycerol, cyclohexane-1,4-dimethanol, phenol, benzyl alcohol, and any combinations thereof.

In some embodiments, the second solvent is a linear $C_1$-$C_4$ alcohol. In some embodiments, the second solvent is methanol, ethanol, propanol, butanol, or a combination thereof. In some embodiments, the second solvent is methanol, ethanol, propanol, or a combination thereof. In some embodiments, the second solvent is methanol. In some embodiments, the alcohol is ethanol. In some embodiments, the second solvent is a branched $C_3$-$C_4$ alcohol. In some embodiments, the second solvent is t-butanol, s-butanol, i-butanol, i-propanol, or any combinations thereof. In some embodiments, the second solvent is a cyclic $C_3$-$C_8$ alcohol. In some embodiments, the second solvent is cyclopropanol, cyclobutanol, cyclopentanol, cyclohexanol, cycloheptanol, cyclohexane-1,4-dimethanol, or any combinations thereof. In some embodiments, the second solvent is cyclohexane-1,4-dimethanol. In some embodiments, the second solvent is a polyol. In some embodiments, the second solvent is selected from ethylene glycol, glycerol, and any combinations thereof. In some embodiments, the second solvent is selected from phenol, benzyl alcohol, and any combinations thereof.

In some embodiments, step (iv) is performed for about 60 mins to about 600 mins. In some embodiments, step (iv) is performed for about 120 mins to about 600 mins. In some embodiments, step (iv) is performed for about 180 mins to about 600 mins. In some embodiments, step (iv) is performed for about 60 mins to about 480 mins. In some embodiments, step (iv) is performed for about 180 mins to about 480 mins. In some embodiments, step (iv) is performed for about 60 mins, 90 mins, 120 mins, 180 mins, 240 mins, 300 mins, 360 mins, 420 mins, 480 mins, 540 mins, or 600 mins. In some embodiments, step (iv) is performed for about 360 min.

In some embodiments, step (iv) is performed at a temperature between about 70° C. to about 100° C. In some embodiments, step (iv) is performed at a temperature between about 70° C. to about 90° C. In some embodiments, step (iv) is performed at a temperature between about 80° C. to about 100° C. In some embodiments, step (iv) is performed at a temperature of about 70° C., about 75° C., about 80° C., about 85° C., about 90° C., about 95° C., or about 100° C. In some embodiments, step (iv) is performed at a temperature of about 85° C.

In some embodiments, the process further comprises step (v) filtrating the terephthalate.

In some embodiments, the process further comprises step (vi) distilling the terephthalate. Alternatively, in some embodiments, the process further comprises step (vi) subliming the terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) adding a glycoxide to the first mixture;
(iii) adding a second solvent;

(iv) admixing; and
(v) filtrating the terephthalate;
thereby isolating the terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) adding a glycoxide to the first mixture;
(iii) adding a second solvent;
(iv) admixing;
(v) filtrating the terephthalate; and
(vi) distilling the terephthalate;
thereby isolating pure terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) adding a glycoxide to the first mixture;
(iii) adding a second solvent;
(iv) admixing;
(v) filtrating the terephthalate; and
(vi) subliming the terephthalate;
thereby isolating pure terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) removing a portion of the first solvent from the first mixture to yield a second mixture;
(iii) adding a glycoxide to the second mixture;
(iv) adding a second solvent; and
(v) admixing;
thereby forming the terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) removing a portion of the second solvent from the first mixture to yield a second mixture;
(iii) adding a glycoxide to the second mixture;
(iv) adding a second solvent;
(v) admixing; and
(vi) filtrating the terephthalate;
thereby isolating the terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) removing a portion of the second solvent from the first mixture to yield a second mixture;
(iii) adding a glycoxide to the second mixture;
(iv) adding a second solvent;
(v) admixing;
(vi) filtrating the terephthalate; and
(vii) distilling the terephthalate;
thereby isolating pure terephthalate.

Also described herein is a process for the depolymerization of polyethylene terephthalate (PET) to form a terephthalate; the process comprising:
(i) admixing the polyethylene terephthalate (PET) with a first solvent to yield a first mixture;
(ii) removing a portion of the second solvent from the first mixture to yield a second mixture;
(iii) adding a glycoxide to the second mixture;
(iv) adding a second solvent;
(v) admixing;
(vi) filtrating the terephthalate; and
(vii) subliming the terephthalate;
thereby isolating pure terephthalate.

CERTAIN TERMINOLOGY

The section headings used herein are for organizational purposes only and are not to be construed as limiting the subject matter described.

Unless defined otherwise, all technical and scientific terms used herein have the same meaning as is commonly understood to which the claimed subject matter belongs. In the event that there are a plurality of definitions for terms herein, those in this section prevail.

It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the term "about" or "approximately" means within 10%, preferably within 10%, and more preferably within 5% of a given value or range.

As used herein, ambient temperature is a colloquial expression for the typical or preferred indoor (climate-controlled) temperature to which people are generally accustomed. It represents the small range of temperatures at which the air feels neither hot nor cold, approximately 21° C. In some embodiments, ambient temperature is 25±5° C. In some embodiments, ambient temperature is 18° C. In some embodiments, ambient temperature is 19° C. In some embodiments, ambient temperature is 20° C. In some embodiments, ambient temperature is 21° C. In some embodiments, ambient temperature is 22° C. In some embodiments, ambient temperature is 23° C. In some embodiments, ambient temperature is 24° C. In some embodiments, ambient temperature is 25° C. In some embodiments, ambient temperature is 26° C. In some embodiments, ambient temperature is 27° C. In some embodiments, ambient temperature is 28° C. In some embodiments, ambient temperature is 29° C. In some embodiments, ambient temperature is 30° C.

As used in this specification and the appended claims, depolymerization, refer to a way of breaking down a polymer to its starting material. It is essentially the opposite of polymerization. In some embodiments, the depolymerization is achieved by glycolysis, methanolysis or hydrolysis, categorized by the depolymerization reactant used, such as glycol, methanol or water, respectively.

As used herein, the term "mol" when referring to PET is the molar amount and is calculated using the molecular weight of the "PET" unit which is 192.17 g/mol.

Definition of standard chemistry terms may be found in reference works, including but not limited to, Carey and Sundberg "Advanced Organic Chemistry 4th Ed." Vols. A (2000) and B (2001), Plenum Press, New York.

EXAMPLES

The following examples are intended to illustrate but not limit the disclosed embodiments.

Example 1: Mono Sodium Glycoxide Formation

Dissolution Step:

Mono ethylene glycol (MEG, 2447.7 g) was added to a 6 L glass reactor and heated to 90° C. while stirring at 230 RPM. Sodium hydroxide (NaOH, 1770.6 g, as micro granules) were slowly added (very exothermic). MEG/NaOH (mol/mol): 1 to 1.2:1. The temperature of the mixture after addition of sodium hydroxide was monitored and recorded). The mixture was stirred (280 RPM) while maintaining the temperature at 150° C. for about 10 minutes (to make sure that all the sodium hydroxide dissolves). The liquid obtained was spread on Pyrex® plates and placed in a vacuum oven (at 130° C. and −30 inches of Hg pressure) for 60 minutes. The vacuum oven chamber was purged with nitrogen and placed back under vacuum. The plates were dried for about 12 hours. Once the catalyst is dry it was removed from the vacuum oven, grinded, and placed again in the vacuum oven (at 130° C. and −30 inches of Hg pressure). The vacuum oven chamber was purged with nitrogen and placed back under vacuum. The catalyst was dried for about 12 hours. Once the catalyst is dried it was removed from the vacuum oven and added to a Pyrex® bottle. Methanol was added (ratio catalyst/MeOH (mol/mol): 0.18:1) and stirred for 30 minutes. The suspension was kept in a flammable cabinet for up to one week.

Example 2: Depolymerization of Polyethylene Terephthalate

Swelling and Rinse:

The polyethylene terephthalate feedstock (10 Kg) was added to a jacketed with a scraped double motion agitation (hermetically closed) reactor. The reactor was purged with nitrogen for 3 minutes. Methanol (6 Kg) was added and the resulting mixture was heated at about 60° C. and stirred at 60 rpm for about 60 minutes. The pressure and temperature were recorded. A portion of the liquid (3.5 Kg) was drained.

Reaction:

The reactor's central agitation was started (155 RPM). The scraper was started (70 RPM). The heat was increased to about 85° C. The glycoxide suspension (973.5 g, 31.5 weight % glycoxide) was added and the mixture was heated and stirred for 5 minutes. The pressure and temperature were recorded. Additional methanol (3.83 Kg) was added and the resulting mixture was reacted for about 360 minutes (after reaching temperature). The mixture was then cooled to 25° C.

Filtration:

The solid was filtered and washed with methanol (4.8 Kg). The filter cake (dimethyl terephthalate) was weighted.

Distillation:

DMT recovery: The cake containing the DMT and the unreacted material was melted at 150° C. The mixture was then evaporated or distilled in a thin film or a distillation column or any evaporation or distillation system at 160° C. under 2 torr of vacuum or 180° C. under 50 torr of vacuum. The DMT was recovered as a solid or as a liquid if the receiving system is heated at 150° C.

MEG recovery: The mother liquor containing the MEG and methanol was passed through an evaporation or distillation system such as a thin film, a distillation column, an evaporator, etc, to remove around 70% of the methanol (at 30° C. under full vacuum). The recovered slurry was then chilled at 3 to −6° C. and filtered. A liquid was recovered and the residual 30% of methanol was removed by evaporation or distillation. The MEG left was then distilled or evaporated at 100° C. under full vacuum.

DMT yields using various amounts of catalysts and different catalysts are shown in the table below. For all examples:

The molar PET amount (calculated using the "PET" unit molecular weight of 192.17 g/mol) was 52 mol;

The Molar amount of methanol was 218 mol;

The temperature was 70° C.;

The Reaction time was 480 mins.

| Catalyst | Catalyst Amount (mol) | Pressure (psi)[1] | DMT Yield (%)[2] |
|---|---|---|---|
| Mono sodium glycoxide | 9.2 | 9 | 99 |
| Sodium methoxide | 9.2 | 13 | 99 |
| Mono sodium glycoxide | 5.5 | 8 | 99 |
| Sodium methoxide | 5.5 | 10 | 98 |
| Mono sodium glycoxide | 3.7 | 8 | 99 |
| Sodium methoxide | 3.7 | 11 | 96 |

[1]pressure generated in hermetically closed reactor.
[2]before DMT distillation.

MEG yields using different catalysts are shown in the table below:

| Catalyst | Catalyst Amount (mol) | Pressure (psi) | Yield of conversion to MEG (%) | Amount of MEG generated (mol) | Amount of MEG in the mother liquor after filtration (mol) | Amount of MEG recovered by one distillation (mol) | MEG Yield (based on the amount found in the mother liquor) |
|---|---|---|---|---|---|---|---|
| Sodium glycoxide | 5.2 | 8 | 99 | 51.5 | 46.7 | 38.7 | 83% |
| Sodium methoxide | 5.2 | 10 | 98 | 51.0 | 46.0 | 32.1 | 70% |

What is claimed is:

1. A process for depolymerization of a polyester to form a terephthalate; the process comprising admixing the polyester, a glycoxide, and at least one solvent comprising methanol.

2. The process of claim 1, wherein the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly(3-hydroxy butyrate-co-3-hydroxyvalerate) (PHBV), polybutylene terephthalate (PBT), polytrimethylene terephthalate (PTT), polyethylene naphthalate (PEN), cutin, or any combinations thereof.

3. The process of claim 1, wherein the terephthalate is obtained in at least about 90 mol % yield.

4. The process of claim 1, wherein the at least one solvent is added to the polyester prior to the addition of the glycoxide.

5. The process of claim 4, wherein the polyester is mixed with the at least one solvent prior to the addition of the glycoxide for about 15 mins to about 120 mins.

6. The process of claim 1, wherein the polyester is mixed with the at least one solvent prior to the addition of the glycoxide at a temperature from about 50° C. to about 100° C.

7. The process of claim 1, wherein the terephthalate is dimethyl terephthalate (DMT).

8. The process of claim 1, wherein the glycoxide is sodium glycoxide.

9. The process of claim 8, wherein the sodium glycoxide is mono sodium glycoxide.

10. The process of claim 9, wherein the mono sodium glycoxide is provided as a suspension.

11. The process of claim 10, wherein the mono sodium glycoxide suspension is prepared by a process comprising:
   a) heating mono ethylene glycol;
   b) adding sodium hydroxide thereby forming mono sodium glycoxide;
   c) drying the mono sodium glycoxide;
   d) suspending the dried mono sodium glycoxide into a suspending solvent; and
   e) aging the suspension.

12. The process of claim 11, wherein step (a) is performed at a temperature from about 70° C. to about 100° C.

13. The process of claim 12, wherein a ratio of mono sodium glycoxide to the suspending solvent is from about 0.05:1 to about 0.5:1 (mol/mol).

14. The process of claim 13, wherein the suspending solvent is methanol.

15. The process of claim 1, wherein a ratio of the glycoxide to the polyester is from about 1:2 to about 1:20 (mol/mol).

16. The process of claim 1, wherein a ratio of the glycoxide to the polyester is from about 1:5 to about 1:20 (mol/mol).

17. The process of claim 1, wherein a ratio of the glycoxide to the polyester is from about 1:10 to about 1:20 (mol/mol).

18. A process for preparing a mono sodium glycoxide suspension; the process comprising:
   a) heating mono ethylene glycol;
   b) adding sodium hydroxide thereby forming mono sodium glycoxide;
   c) drying the mono sodium glycoxide;
   d) suspending the dried mono sodium glycoxide into a suspending solvent; and
   e) aging the suspension.

* * * * *